United States Patent [19]
Chen et al.

[11] Patent Number: 5,877,329
[45] Date of Patent: Mar. 2, 1999

[54] PALLADIUM CATALYZED INDOLIZATION

[75] Inventors: Cheng-Yi Chen, Colonia; Robert D. Larsen, Bridgewater, both of N.J.

[73] Assignee: Merck & Co., Inc., Rahway, N.J.

[21] Appl. No.: 907,407

[22] Filed: Aug. 7, 1997

Related U.S. Application Data

[60] Provisional application No. 60/023,872 Aug. 13, 1996 and provisional application No. 60/029,344 Oct. 31, 1996.

[51] Int. Cl.$^6$ .................................................. C07D 209/04
[52] U.S. Cl. .............................................. 548/491
[58] Field of Search ............................................ 548/491

[56] References Cited

U.S. PATENT DOCUMENTS 5,298,520  3/1994  Baker et al. .
5,567,824  10/1996  Chen et al. .

FOREIGN PATENT DOCUMENTS

| 0 497 512 | 5/1992 | European Pat. Off. . |
| 0 548 813 A1 | 6/1993 | European Pat. Off. . |
| WO 94/02476 | 3/1994 | WIPO . |
| WO 95/32197 | 11/1995 | WIPO . |

OTHER PUBLICATIONS

Astleford, et al. "Synthesis of 1–Alkyly . . . " J. Org. Chem. vol. 54, pp. 731–732, 1989.
Wensbo, et al. "Palladium–Catalysed Synthesis of Heterocondensed Pyrroles" Tetrahedron Letters, vol. 34, No. 17 pp. 2823–2826, 1993.
Jeschke et al, "A Novel Approach to Bz–Substituted Thyptophans . . . "Tetrahedron Letters, vol. 34, No. 40, pp. 6471–6474 (1993).
Larock et al., "Synthesis of Indoles via Palladium . . . " J. AM. Chem. Soc., vol. 113, pp. 6689–6690, 1991.
Luo et al., "Heterocycles" Chemical Abstracts, vol. 116, No. 19, AB. No. 19, AB. No. 194092, 1991.
Chen et al., Tetrahedron Letters, vol. 35, No. 38, pp. 6981–6984 (1994).
"Synthesis of the 5 HTID Receptor Agonist . . . ".
Chen et al., "Improved Fischer Indole Reaction . . . " J. Org Chem. vol. 59, 3738 (1994).
Iida, et al., "Intramolecular Cyclization of Enaminones . . . " J. Org. Chem. vol. 45, 2938–2942 (1980).
Sakamoto, et al., "Condensed Heteroaromatic Ring Systems . . . " Synthesis, pp. 215–218, (1990).
Synthesis Mar. 1990, pp. 215–218. Sakamoto et al. Condensed Heteroaromatic Ring System.

*Primary Examiner*—Johann Richter
*Assistant Examiner*—Ebenezer Sackey
*Attorney, Agent, or Firm*—Philippe L. Durette; Catherine D. Fitch; Melvin Winokur

[57] ABSTRACT

Indoles of structural formula (III):

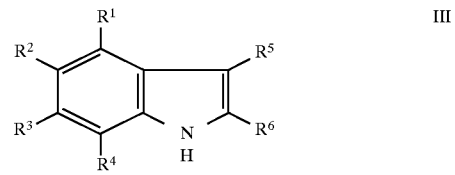

are synthesized by the palladium-catalyzed coupling/ring closure of a 2-halo or 2-trifluoromethylsulfonyloxy aniline and an alkyl ketone derivative. The process is particularly useful to form indoles containing acid-labile substituents such as triazole, acetyl, ketal, cyano, and carbamate, or indoles having a facile leaving group in the benzyl position. The advantages of the present process are that it does not require the use of triphenyl phosphine or tetrabutyl ammonium chloride or lithium chloride.

18 Claims, No Drawings

PALLADIUM CATALYZED INDOLIZATION

This application claims the benefit of provisional application No. 60/023,872 filed Aug. 13, 1996 and provisional application No. 60/029,344 filed Oct. 31, 1996.

BACKGROUND OF THE INVENTION

The present invention relates to the preparation of indoles from the palladium catalyzed reaction of 2-halo- and 2-trifluoromethylsulfonyloxy-anilines and ketones. In one embodiment of the present invention, substituted alkyl ketones are employed. This embodiment is particularly useful in preparing 2, 3, di-substituted indole derivatives, useful in the preparation of indomethacin and certain lipoxygenase inhibitors. Thus, the process of the present invention is useful in preparing biologically active compounds.

Generally, indoles are prepared via the Fischer-indole reaction. For example, Chen et al., *J. Org. Chem.*, 59:3738 (1994) disclose the preparation of N,N-dimethyl tryptamines from 4-substituted hydrazines and dimethylaminobutyraldehyde dimethyl acetal using 4% $H_2SO_4$. However, the yields are often low, particularly for compounds having triazole substitution. Benzyltriazoles are unstable to the Fischer indole reaction conditions, which generally lead to polymerization of the triazole moiety, and the production of oligomers.

Chen et al., *Tet. Lett.* 35:6981 (1994) describe basic/neutral coupling to form indoles employing hydrazines. Hydrazines are inherently less stable than the amines (anilines) employed in the present invention.

In contrast, the present invention provides for a robust process that occurs under mild conditions.

Iida et al., *J. Org. Chem.* 45:2938–2942 (1980) describe intramolecular cyclization of 3-((2-bromoaryl)amino) cyclohex-2-en-1-ones with catalytic palladium in the presence of triphenyl phosphine, as well as the reaction of aryl amines with β-diketones to form the corresponding secondary enaminone followed by N-ethylation to form the corresponding tertiary enaminones and subsequent intramolecular cyclization in the presence of equimolar palladium acetate.

Sakamota et al., *Synthesis*, p. 215–218 (1990), describe palladium-catalyzed cyclization of β-(2-halophenyl)amino substituted α,β-unsaturated ketones and esters to produce 2,3-disubstituted indoles. The procedure of Sakamota et al., also employs phosphine. Further, the Sakamoto method requires a 1,3-diketone. The process of the present invention employs a mono-ketone.

Indole is a common feature of a variety of natural products, many of which possess potent biological activities. Hence, indoles are attractive synthetic targets. When substituted alkyl ketones are employed in the process of the present invention, the present invention has particular application in the synthesis of 2,3-disubstituted indoles, including the precursor to indomethacin, shown below.

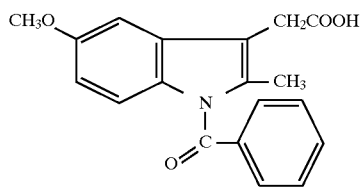

Indomethacin

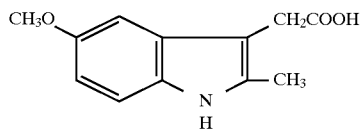

Indomethacin precursor

When cyclic ketones are employed in the process of the present invention, the present invention has particular application in the synthesis of tetrahydrocarbazole derivatives and homologs and analogs thereof. In particular, the precursor to the antidepressant iprindole may be made according to the process of the present invention.

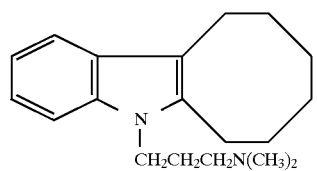

Iprindole

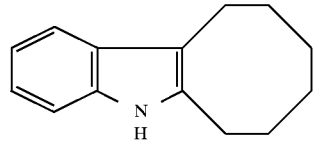

Iprindole precursor

Thus, the present invention also provides for an efficient and cost-effective synthesis of pharmaceutically active indole derivatives useful in the treatment of disease.

SUMMARY OF THE INVENTION

We have found that indoles of structural formula (III):

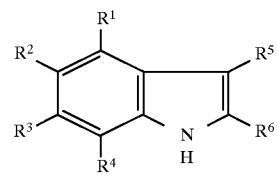

can be cost-effectively synthesized in high yield by the palladium-catalyzed coupling/ring closure of a 2-halo or 2-trifluoromethylsulfonyloxy-aniline and an alkyl ketone derivative. The process of the present invention is particularly useful to form indoles containing acid-labile substituents such as triazole, acetyl, ketal, cyano, and carbamate, or indoles having a good leaving group in the benzyl position. The advantages of the present process are that it does not require the use of triphenyl phosphine or tetrabutyl ammonium chloride or lithium chloride.

By this invention, there is provided a process comprising the step of contacting a compound of Structure I with a compound of Structure II to form a compound of Structure III:

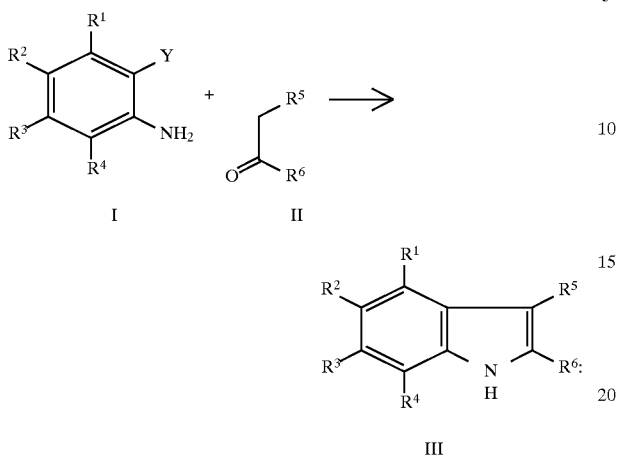

wherein Y is selected from Br, I, and triflate, and $R^1$, $R^2$, $R^3$, $R^4$, $R^5$, and $R^6$ are each substituents that will not interfere with the reaction conditions, provided that R6 is not H.

Still further, the present invention is also directed to the novel intermediates of structural formulae (IV) and (V).

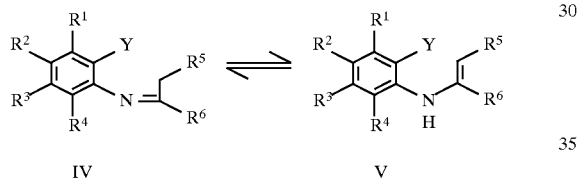

DETAILED DESCRIPTION OF THE INVENTION

More particularly, the present invention relates to the process comprising the step of contacting a compound of Structure I with a compound of Structure II to form a compound of Structure III:

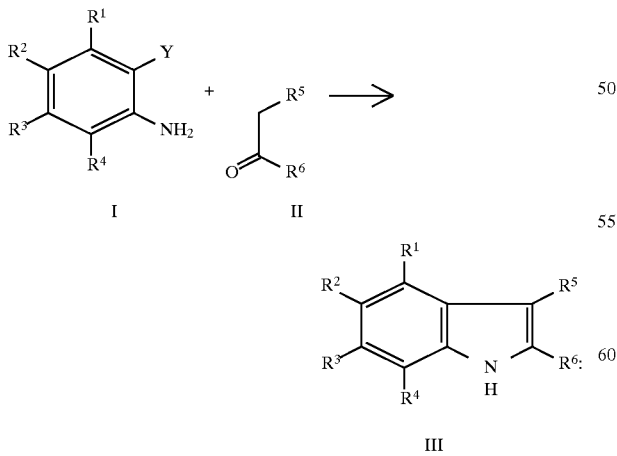

Y is selected from Br, I and triflate;
$R^1$, $R^2$, $R^3$ and $R^4$ are each independently selected from:

(1) hydrogen;

(2) 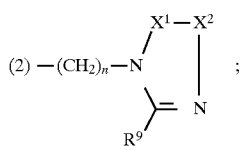 ;

(3) $C_{1-6}$ alkyl;
(4) —$(CH_2)_n$—Z wherein Z represents:
  (a) fluoro,
  (b) cyano,
  (c) triazole,
  (d) nitro,
  (e) trifluoromethyl,
  (f) —$OR^7$,
  (g) —$OCOR^7$,
  (h) —$OCONR^7R^8$,
  (i) —$OCH_2CN$,
  (j) —$OCH_2CONR^7R^8$,
  (k) —$SR^7$, provided that $R^7$ is not H,
  (l) —$SOR^7$,
  (m) —$SO_2R^7$,
  (n) —$SO_2NR^7R^8$,
  (o) —$NR^7R^8$,
  (p) —$NR^7COR^8$,
  (q) —$NR^7CO_2R^8$,
  (r) —$NR^7SO_2R^8$,
  (s) —$COR^7$,
  (t) —$CO_2R^7$,
  (u) —$CONR^7R^8$,
or Z is a group of formula (Za), (Zb), (Zc), or (Zd):

 (Za)

 (Zb)

 (Zc)

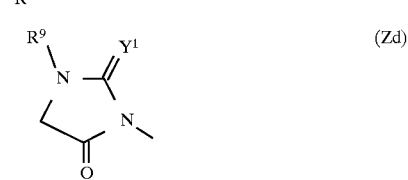 (Zd)

or Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole;

$R^5$ is selected from:
  (1) hydrogen,
  (2) $C_{1-6}$ alkyl,
  (3) —$CO_2C_{1-6}$ alkyl,
  (4) 1,3-dioxaspiro,
  (5) —$S(O)_pC_{1-6}$ alkyl, and (6) $C_{1-6}$ alkyl substituted with $R^{10}$;
$R^6$ is selected from:
(1) $C_{1-6}$ alkyl,
(2) —$CO_2C_{1-6}$ alkyl,
(3) 1,3-dioxaspiro,
(4) —$S(O)_pC_{1-6}$ alkyl, and
(5) $C_{1-6}$ alkyl substituted with $R^{10}$;
$R^7$ and $R^8$ are each independently selected from:
(1) hydrogen,
(2) $C_{1-6}$ alkyl,
(3) trifluoromethyl,
(4) phenyl, optionally substituted with one or more $R^{13}$ substituents,
(5) methylphenyl, optionally substituted with one or more $R^{13}$ substituents, and
(6) an aryl$C_{1-6}$alkyl- or heteroaryl $C_{1-6}$alkyl- group, optionally substituted with one or more $R^{13}$ substituents, or
$R^7$ and $R^8$ when linked through a nitrogen atom, together represent the residue of an optionally substituted azetidine, pyrrolidine, piperidine, morpholine or piperazine ring, optionally substituted with one or more $R^{13}$ substituents;
$R^9$ is selected from:
(1) hydrogen, and
(2) $C_{1-4}$ alkyl;
$R^{10}$ is selected from:
(1) halogen,
(2) cyano,
(3) trifluoromethyl,
(4) $C_{1-6}$alkyl,
(5) halo$C_{1-6}$alkyl-,
(6) aryl,
(7) triazolyl,
(8) tetrazolyl,
(9) $C_{1-6}$alkyl-tetrazolyl-,
(10) hydroxy,
(11) $C_{1-6}$alkoxy-,
(12) $C_{1-6}$alkylthio-,
(13) $C_{1-6}$alkoxycarbonyl-,
(14) $C_{1-6}$alkylcarbonyl-,
(15) $C_{1-6}$alkylsulphonyl-,
(16) arylsulfonyl-,
(17) amino-,
(18) $C_{1-6}$alkylamino-,
(19) di$C_{1-6}$alkylamino-,
(20) di$C_{1-6}$alkylaminomethyl-,
(21) $C_{1-6}$alkylcarbonylamino-,
(22) arylcarbonylamino-,
(23) $C_{1-6}$alkoxycarbonylamino-,
(24) N—$C_{1-6}$alkyl-N—$C_{2-6}$alkoxyamino-,
(25) carbonylamino-,
(26) mono- or diarylaminocarbonylamino-,
(27) pyrrolidinylcarbonylamino-,
(28) piperidinylcarbonylamino-,
(29) aminocarbonyl-,
(30) aminocarbonylamino-,
(31) $C_{1-6}$alkylaminocarbonyl-,
(32) $C_{1-6}$alkylaminocarbonylamino-,
(33) di$C_{1-6}$alkylaminocarbonyl-,
(34) di$C_{1-6}$alkylaminocarbonylamino-,
(35) pyrrolidinylcarbonylamino-,
(36) piperidinylcarbonylamino-,
(37) aminosulfonyl-,
(38) $C_{1-6}$alkylaminosulfonyl-,
(39) $C_{1-6}$alkylsulfonylamino-,
(40) $C_{1-6}$alkylsulfonylaminomethyl-,
(41) arylsulfonylamino-,
(42) di$C_{1-6}$alkylaminosulfonyl-,
(43) aminosulphonylmethyl-,
(44) $C_{1-6}$alkylaminosulfonylmethyl-, and
(45) di$C_{1-6}$alkylaminosulfonylmethyl-,
(46) —$(CH_2)_mOR^{11}$,
(47) —$(CH_2)_mSR^{11}$, provided that $R^{11}$ is not H,
(48) —$(CH_2)_mSOR^{11}$
(49) —$(CH_2)_mSO_2R^{11}$,
(50) —$(CH_2)_mNR^{11}R^{12}$,
(51) =O, and
(52) carbonyloxy-,

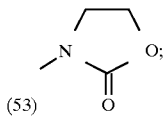
(53)

$R^{11}$ and $R^{12}$ are each independently selected from
(1) hydrogen,
(2) $C_{1-6}$alkyl,
(3) $C_{3-7}$cycloalkyl,
(4) $C_{3-7}$cycloalkyl$C_{1-6}$alkyl-,
(5) indanyl,
(6) aryl,
(7) aryl$C_{1-6}$alkyl-,
(8) $C_{3-7}$heterocycloalkyl-,
(9) $C_{3-7}$heterocycloalkyl$C_{1-6}$alkyl-,
(10) heteroaryl, and
(11) heteroaryl$C_{1-6}$alkyl-;
$R^{13}$ is selected from:
(1) $C_{1-6}$alkyl,
(2) aryl$C_{1-6}$alkyl-,
(3) $C_{1-6}$alkoxy-,
(4) $C_{1-6}$alkyoxycarbonyl-, and
(5) $C_{1-6}$alkylaminocarbonyl;
$X^1$ and $X^2$ are each independently selected from ring nitrogen or ring carbon atoms;
$X^3$ is selected from the group consisting of oxygen, sulfur, —NH— or methylene;
$Y^1$ is oxygen or sulfur;
n is an integer independently selected at each occurrence from 0 to 4;
m is an integer selected independently at each occurrence from 0 to 4, and
p is an integer selected independently at each occurrence from 0, 1 and 2.

The process is preferably carried out in a dry organic solvent inert for the starting materials at a temperature range of 90°–120° C. in the presence of a palladium catalyst, and in the presence of a proton acceptor which is most preferably an organic amine compound.

Where Z in the compounds of formulae I and III above represents a five-membered heteroaromatic ring, this ring may be optionally substituted by one or, where possible, two substituents. As will be appreciated, where Z represents oxadiazole, thiadiazole or tetrazole ring, only one substituent will be possible; otherwise, one or two optional substituents may be accommodated around the five-membered heteroaromatic ring Z. Examples of suitable substituents on the five-membered heteroaromatic ring Z include $C_{1-6}$ alkyl, $C_{2-6}$alkenyl, $C_{2-6}$alkynyl, $C_{3-7}$ cycloalkyl, aryl, aryl $C_{1-6}$ alkyl, $C_{3-7}$ heterocycloalkyl, heteroaryl; $C_{1-6}$ alkyl, $C_{1-6}$alkoxy, $C_{1-6}$alkylthio, amino, $C_{1-6}$alkylamino, di$C_{1-6}$alkylamino, halogen, cyano, and trifluoromethyl.

Combinations of substituents and/or variables are permissible only if such combinations result in stable compounds.

In one embodiment of the present invention, $R^1$, $R^3$, and $R^4$ are each hydrogen and $R^2$, $R^5$, $R^6$ and Y are as defined above.

The term "triflate" or "OTf" refers to the trifluoromethane sulfonyloxy group.

When an amine is included as a substituent on a compound in the present invention, in order to optimize the conditions of the reaction and to obtain better yields, the amine may have to be protected, as is known in the art, and the protecting group removed following the coupling reaction.

When a carbonyl group is included as a substituent on a compound in the present invention, in order to optimize the conditions of the reaction and to obtain better yields, the carbonyl group may have to be protected, as is known in the art, and the protecting group removed following the coupling reaction.

As used herein "alkyl", particularly the expression "$C_{1-6}$ alkyl", includes methyl and ethyl groups and straight chained or branched propyl, butyl, pentyl and hexyl groups. Particular alkyl groups are methyl, ethyl, n-propyl, isopropyl and t-butyl. Derived expressions such as $C_{1-6}$alkyoxy, $C_{1-6}$alkylthio, and $C_{1-6}$alkyl amino are to be construed accordingly.

Typical $C_{3-7}$ cycloalkyl groups include cyproyl, cyclobutyl, cyclopentyl and cyclohexyl.

Typical aryl groups include phenyl and naphthyl. More particularly, aryl is phenyl.

Particular indanyl groups include indan-1-yl and indan-2-yl.

Particular aryl$C_{1-6}$alkyl groups include benzyl, phenylethyl, phenylpropyl and naphthylmethyl.

Suitable heterocycloalkyl groups include azetidinyl, pyrrolidinyl, piperidyl, piperazinyl and morpholinyl.

Suitable heteroaryl groups include pyridyl, quinolyl, soquinolyl, pyridazinyl, pyrimidinyl, pyrazinyl, pyranyl, furyl, enzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, and tetrazolyl groups.

The expression "heteroaryl $C_{1-6}$alkyl" as used herein includes furylmethyl, furylethyl, thienylmethyl, thienylethyl, oxazolylmethyl, oxazolylethyl, thiazolylmethyl, thiazolylethyl., imidiazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridylmethyl, pyridylethyl, pyridinylmethyl, pyrazinylmethyl, quinolylmethyl, and isoquinolylmethyl.

The term "halogen" as used herein includes fluorine, chlorine, bromine and iodine, especially fluorine, unless otherwise specified.

The process of the present invention is preferably carried out in a dry organic solvent inert for the starting materials in the presence of a palladium catalyst, and in the presence of an inorganic or organic base which is not a "catalyst poison". Preferably, the present process is carried out at an elevated temperature.

In the process of the present invention, Structure I is coupled with Structure II to form Structure III via a palladium catalyzed reaction in a dry inert organic solvent containing a palladium catalyst and in the presence of a proton acceptor, being an aromatic amine, alkylamine or inorganic base, which is not a "catalyst poison," at a temperature of about 90°–120° C.

The organic solvent useful in the process of the present invention must be one in which Structure I, Structure II and the palladium catalyst are soluble and compatible and is chemically inert under the reaction conditions. Preferred are DMSO (dimethylsulfoxide) and amide solvents such as DMF (dimethylformamide), DMAC (N,N-dimethylacetamide), and NMP (N-methyl-pyrrolidinone). Most preferred is DMF.

The alkyl ketone of structural formula (II) is generally employed in excess based on the 2-halo- or 2-(OTf)- aniline of structural formula (I). A useful range is about 1.0 to 3 fold excess, based on the 2-halo- or 2-(OTf)- aniline of structural formula I. The alkyl ketone may be favorably employed at a two-fold excess, based on the 2-halo- or 2-(OTf)- aniline of structural formula I.

The proton acceptor useful in the process of the present invention is a basic compound which can be organic or inorganic and acts as a proton acceptor and is not a "catalyst poison". By the term "catalyst poison" is meant interaction with the catalyst to inhibit its catalytic activity and prevent the coupling/ring closure between structures I and II from occurring. Suitable classes of proton acceptors include alkylamines, aromatic amines, heterocyclic amines, and phosphates. Alkylamines are the preferred proton acceptor in the process of the present invention. Particular alkylamines that may be employed include: DABCO (1,4-diazabicyclo[2.2.2]octane), 2,2,6,6-tetramethyl piperidine quinuclidine, t-butylamine, and di-t-butyl-amine. DABCO is particularly preferred because it reduces the appearance of impurities in the reaction because it is resistant to oxidation to the imine in the reaction conditions of the process of the present invention.

The proton acceptor is generally employed in excess based on the 2-halo- or 2-(OTf)- aniline of structural formula (I). A useful range is about 2 to 4 fold excess, based on the 2-halo- or 2-(OTf)- aniline of structural formula (I). The proton acceptor may be favorably employed at a three-fold excess, based on the 2-halo- or 2-(OTf)- aniline of structural formula (I).

The palladium catalyst useful in the reaction can be selected from the following classes: Pd alkanoates, Pd acetonates, Pd halides, Pd halide complexes, Pd-benzylidine acetone complexes, as well as triaryl phosphine Pd complexes. Representative examples include, but are not limited to: Pd(II) acetate, Pd(II) acetylacetonate, Pd(O)bis-dibenzylidene acetone ("dba"), Pd(II) bromide, Pd(II) chloride, Pd(II) iodide, Pd(II) sulfate, Pd(II)trifluoroacetate, Pd(II) $Cl_2(CH_3CN)_2$, $Pd_2$ $(dba)_3$, and Pd(II)$Cl_2(PhCN)_2$. A useful catalyst is palladium acetate.

The palladium catalyst is employed in an amount of about 0.5 to 5 mole percent based on the 2-halo- or 2-(OTf)- aniline of structural formula I. A useful range is about 2 to 3 mole percent of palladium catalyst, based on the 2-halo- or 2-(OTf)- aniline of structural formula I.

A dehydrating agent, such as magnesium sulfate or molecular sieves may also be favorably employed in the process of coupling Structure I with Structure II to form Structure III according to the present invention.

The reaction is carried out in the temperature range of 90° to 120° C. A useful temperature is about 100°–105° C. Generally, the reaction is carried out under a dry, inert atmosphere at atmospheric pressure. It is useful to carry out the reaction under a nitrogen atmosphere.

The progress of the reaction may be monitored by means known in the art, including thin-layer silica gel chromatography (TLC), high pressure liquid chromatography (HPLC), gas chromatography (GC), and nuclear magnetic resonance spectroscopy (NMR). Preferably HPLC or TLC is employed, most preferably HPLC. When the reaction is complete, generally in 8 to 72 hours, the reaction mixture is cooled to room temperature and the product is separated by traditional means, e.g. by taking up with organic solvent, such as isopropyl acetate and washing with water and/or other aqueous solutions. The product may then be purified by means known in the art, including preparative thin-layer silica gel chromatography, silica gel chromatography, HPLC, crystallization, and solid-phase extraction. Preferably, the product is purified by silica gel chromatography or crystallization.

Particular compounds according to structural formula (I) that may be made according to the process of the present invention include:

Preferred compounds that may be prepared according to the process of the present invention are:

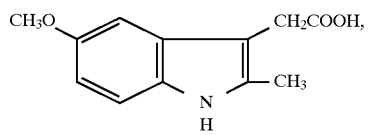

and

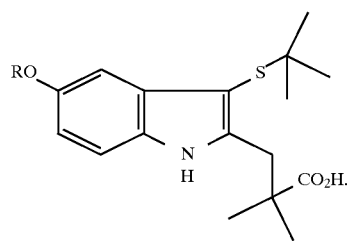

Still further, the present invention is also directed to the novel intermediates of structural formulae (IV) and (V).

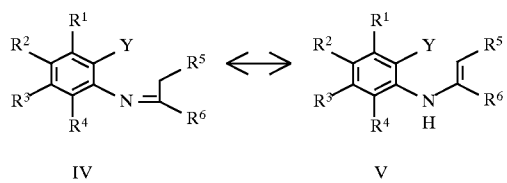

wherein $R^1$, $R^2$, $R^3$, $R^4$, $R^5$, $R^6$, and Y are as defined above.

The 2-halo and 2-(OTf)- anilines and alkyl ketones employed in the processes of the present invention may be synthesized according to procedures well-known in the art, and many are available commercially.

The following examples are not intended to be limitations on the scope of the instant invention in any way, and they should not be so construed. Furthermore, the compounds described in the following examples are not to be construed as forming the only genus that is considered as the invention, and any combination of the compounds or their moieties may itself form a genus. Those skilled in the art will readily understand that known variations of the conditions and processes of the following preparative procedures can be used to prepare these compounds.

EXAMPLE 1

Preparation of Indomethacin Precursor

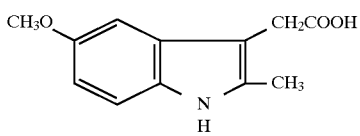

A mixture of 4-methoxy-2-iodoaniline (10 mmol), 4-oxo-pentanoic acid (15 mmol), DABCO (30 mmol) and Pd(OAc)$_2$ (0.5 mmol) in dry DMF (30 mL) are degassed via vacuum/nitrogen and heated to 105° C. The mixture is heated at 105° C. until the completion of the reaction. The mixture is cooled to room temperature and partitioned between 150 mL of isopropyl acetate (IPAc) and 50 mL of acid (2N HCl). The organic layer is separated, washed with 50 mL of brine and concentrated in vacuum to dryness. The residues are chromatographed.

EXAMPLE 2

Preparation of:

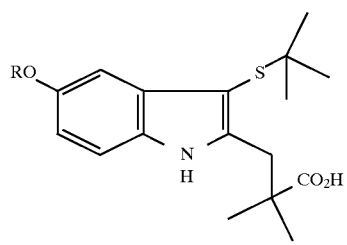

R is-2-quinolinylmethyl.

A mixture of 4-(2-quinolinyl)-methoxy-2-iodoaniline (10 mmol), methyl 5-t-butylthio-2,2-dimethyl-4-oxo-pentanoate (15 mmol), DABCO (30 mmol) and Pd (OAc)$_2$ (0.5 mmol) in dry DMF (30 mL) are degassed via vacuum/nitrogen and heated to 105° C. The mixture is cooled to room temperature and partitioned between 150 mL of isopropyl acetate (IPAc) and 50 mL of acid (2N HCl). The organic layer is separated, washed with 50 mL of brine and concentrated under vacuum to dryness. The residues are chromatographed.

EXAMPLE 3

Preparation of:

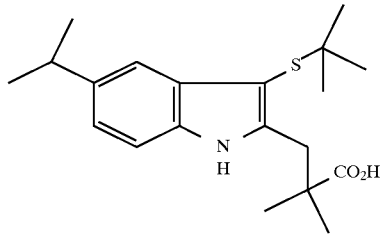

A mixture of 4-isopropyl-2-iodoaniline (10 mmol), methyl 5-t-butylthio-2,2-dimethyl-4-oxo-pentanoate (15 mmol), DABCO (30 mmol) and Pd (OAc)$_2$ (0.5 mmol) in dry DMF (30 mL) are degassed via vacuum/nitrogen and heated to 105° C. The mixture is cooled to room temperature and partitioned between 150 mL of isopropyl acetate (IPAc) and 50 mL of acid (2N HCl). The organic layer is separated, washed with 50 mL of brine and concentrated under vacuum to dryness. The residues are chromatographed.

While the invention has been described and illustrated with reference to certain particular embodiments thereof, those skilled in the art will appreciate that various changes, modifications and substitutions can be made therein without departing from the spirit and scope of the invention. It is intended, therefore, that the invention be defined by the scope of the claims which follow and that such claims be interpreted as broadly as is reasonable.

What is claimed is:

1. A process for preparing a compound of structural formula III

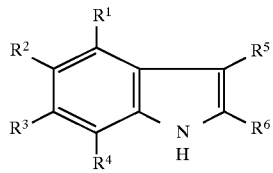

III comprising reacting a compound of structural formula I with a compound of structural formula II:

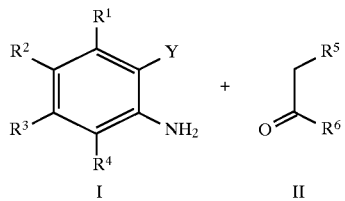

I  II in the presence of a palladium catalyst and a proton acceptor, wherein Y is selected from Br, I, and triflate; $R^1$, $R^2$, $R^3$ and $R^4$ are each independently selected from:

(1) hydrogen;

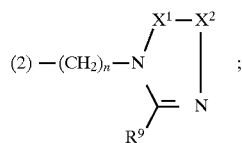

(3) $C_{1-6}$ alkyl;

(4) —(CH$_2$)$_n$—Z wherein Z represents:
(a) fluoro,
(b) cyano,
(c) triazole,
(d) nitro,
(e) trifluoromethyl,
(f) —OR$^7$,
(g) —OCOR$^7$,
(h) —OCONR$^7$R$^8$,
(i) —OCH$_2$CN,
(j) —OCH$_2$CONR$^7$R$^8$,
(k) —SR$^7$, provided that R$^7$ is not H,
(l) —SOR$^7$,
(m) —SO$_2$R$^7$,
(n) —SO$_2$NR$^7$R$^8$,
(o) —NR$^7$R$^8$,
(p) —NR$^7$COR$^8$,
(q) —NR$^7$CO$_2$R$^8$,
(r) —NR$^7$SO$_2$R$^8$,
(s) —COR$^7$,
(t) —CO$_2$R$^7$,
(u) —CONR$^7$R$^8$, or Z is a group of formula (Za), (Zb), (Zc), or (Zd):

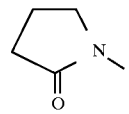 (Za)

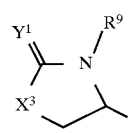 (Zb)

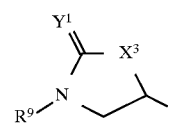 (Zc)

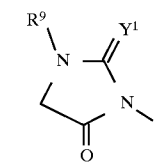 (Zd)

or Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole;

$R^5$ is selected from:
(1) hydrogen,
(2) $C_{1-6}$ alkyl,
(3) —CO$_2$C$_{1-6}$alkyl,
(4) 1,3-dioxaspiro,
(5) —S(O)$_p$C$_{1-6}$ alkyl, and
(6) $C_{1-6}$ alkyl substituted with $R^{10}$;

$R^6$ is selected from:
(1) $C_{1-6}$ alkyl,
(2) —CO$_2$C$_{1-6}$alkyl,
(3) 1,3-dioxaspiro,
(4) —S(O)$_p$C$_{1-6}$ alkyl, and
(5) $C_{1-6}$ alkyl substituted with $R^{10}$;

$R^7$ and $R^8$ are each independently selected from:
(1) hydrogen,
(2) $C_{1-6}$ alkyl, (3) trifluoromethyl,
(4) phenyl, optionally substituted with one or more $R^{13}$ substituents,
(5) methylphenyl, optionally substituted with one or more $R^{13}$ substituents, and
(6) an aryl$C_{1-6}$alkyl- or heteroaryl $C_{1-6}$alkyl- group optionally substituted with one or more $R^{13}$ substituents, or $R^7$ and $R^8$ when linked through a nitrogen atom, together represent the residue of an optionally substituted azetidine, pyrrolidine, piperidine, morpholine or piperazine ring, optionally substituted with one or more $R^{13}$ substituents;

$R^9$ is selected from:
(1) hydrogen, and
(2) $C_{1-4}$ alkyl;

$R^{10}$ is selected from:
(1) halogen,
(2) cyano,
(3) trifluoromethyl,
(4) $C_{1-6}$alkyl,
(5) halo$C_{1-6}$alkyl-,
(6) aryl,
(7) triazolyl,
(8) tetrazolyl,
(9) $C_{1-6}$alkyl-tetrazolyl-,
(10) hydroxy,
(11) $C_{1-6}$alkoxy-,
(12) $C_{1-6}$alkylthio-,
(13) $C_{1-6}$alkoxycarbonyl-,
(14) $C_{1-6}$alkylcarbonyl-,
(15) $C_{1-6}$alkylsulphonyl-,
(16) arylsulfonyl-,
(17) amino-,
(18) $C_{1-6}$alkylamino-,
(19) di$C_{1-6}$alkylamino-,
(20) di$C_{1-6}$alkylaminomethyl-,
(21) $C_{1-6}$alkylcarbonylamino-,
(22) arylcarbonylamino-,
(23) $C_{1-6}$alkoxycarbonylamino-,
(24) N—$C_{1-6}$alkyl-N—$C_{2-6}$alkoxyamino-,
(25) carbonylamino-,
(26) mono- or diarylaminocarbonylamino-,
(27) pyrrolidinylcarbonylamino-,
(28) piperidinylcarbonylamino-,
(29) aminocarbonyl-,
(30) aminocarbonylamino-,
(31) $C_{1-6}$alkylaminocarbonyl-,
(32) $C_{1-6}$alkylaminocarbonylamino-,
(33) di$C_{1-6}$alkylaminocarbonyl-,
(34) di$C_{1-6}$alkylaminocarbonylamino-,
(35) pyrrolidinylcarbonylamino-,
(36) piperidinylcarbonylamino-,
(37) aminosulfonyl-,
(38) $C_{1-6}$alkylaminosulfonyl-,
(39) $C_{1-6}$alkylsulfonylamino-,
(40) $C_{1-6}$alkylsulfonylaminomethyl-,
(41) arylsulfonylamino-,
(42) di$C_{1-6}$alkylaminosulfonyl-,
(43) aminosulphonylmethyl-,
(44) $C_{1-6}$alkylaminosulfonylmethyl-, and
(45) di$C_{1-6}$alkylaminosulfonylmethyl-,
(46) —$(CH_2)_m OR^{11}$,
(47) —$(CH_2)_m SR^{11}$, provided that $R^{11}$ is not H,
(48) —$(CH_2)_m SOR^{11}$
(49) —$(CH_2)_m SO_2R^{11}$,
(50) —$(CH_2)_m NR^{11}R^{12}$,
(51) =O, and
(52) carbonyloxy-,

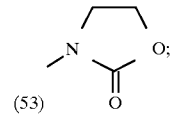
(53)

$R^{11}$ and $R^{12}$ are each independently selected from
(1) hydrogen,
(2) $C_{1-6}$alkyl,
(3) $C_{3-7}$cycloalkyl,
(4) $C_{3-7}$cycloalkyl$C_{1-6}$alkyl-,
(5) indanyl,
(6) aryl,
(7) aryl$C_{1-6}$alkyl-,
(8) $C_{3-7}$heterocycloalkyl-,
(9) $C_{3-7}$heterocycloalkyl$C_{1-6}$alkyl-,
(10) heteroaryl, and
(11) heteroaryl$C_{1-6}$alkyl-;

$R^{13}$ is selected from:
(1) $C_{1-6}$alkyl,
(2) aryl$C_{1-6}$alkyl-,
(3) $C_{1-6}$alkoxy-,
(4) $C_{2-6}$alkyoxycarbonyl-, and
(5) $C_{1-6}$alkylaminocarbonyl;

$X^1$ and $X^2$ are each independently selected from ring nitrogen or ring carbon atoms;

$X^3$ is selected from the group consisting of oxygen, sulfur, —NH— or methylene;

$Y^1$ is oxygen or sulfur;

n is an integer independently selected at each occurrence from 0 to 1;

m is an integer selected independently at each occurrence from 0 to 4, and p is an integer selected independently at each occurrence from 0, 1 and 2.

2. The process according to claim 1 wherein $R^1$, $R^3$, and $R^4$ are each hydrogen.

3. The process according to claim 1 wherein the palladium catalyst is selected from: a palladium alkanoate, a palladium acetonate, a palladium halide, a palladium halide complex, a palladium-benzylidine acetone complex and a triarylphosphine palladium complex.

4. The process according to claim 3 wherein the palladium catalyst is selected from:

Pd(II) acetate, Pd(III) acetylacetonate, Pd(O)bis-dibenzylidene acetone ("dba"), Pd(II) bromide, Pd(II) chloride, Pd(II) iodide, Pd(II) sulfate, Pd(II) trifluoroacetate, Pd(II) $Cl_2(CH_3CN)_2$, $Pd_2$ $(dba)_3$, and Pd(II)$Cl_2$(PhCN)$_2$.

5. The process according to claim 4 wherein the palladium catalyst is Pd(II) acetate.

6. The process according to claim 1 wherein the proton acceptor does not interact with the palladium catalyst to inhibit its catalytic activity.

7. The process according to claim 6 wherein the proton acceptor is selected from:

(a) an alkylamine,
(b) an aromatic amine,
(c) a heterocyclic amine, and
(d) a phosphate.

8. The process according to claim 7 wherein the proton acceptor is an alkylamine.

9. The process according to claim 8 wherein the alkylamine is selected from:
(a) 1,4-diazobicyclo[2.2.2]octane,
(b) 2,2,6,6-tetramethylpiperidine
(c) quinuclidine,
(d) t-butylamine, and
(e) di-t-butylamine.

10. The process according to claim 9 wherein the alkylamine is 1,4-diazobicyclo[2.2.2]octane.

11. The process according to claim 1 wherein the reaction is carried out in a dry organic solvent inert for the starting materials.

12. The process according to claim 11 wherein the solvent is selected from:
(a) DMSO,
(b) DMF,
(c) DMAC, and
(d) NMP.

13. The process according to claim 12 wherein the solvent is DMF.

14. The process according to claim 1 wherein the reaction is carried out at a temperature of 90° C. to 120° C.

15. The process according to claim 14 wherein the temperature is 100° C. to 105° C.

16. The process according to claim 1 wherein the compound according to structural formula III is selected from:

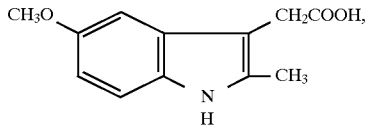

(a)

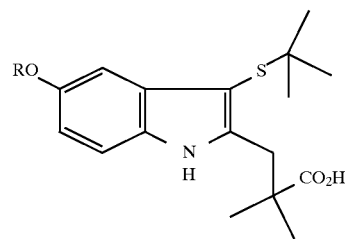

(b)

wherein: R is -2-quinolinylmethyl, and

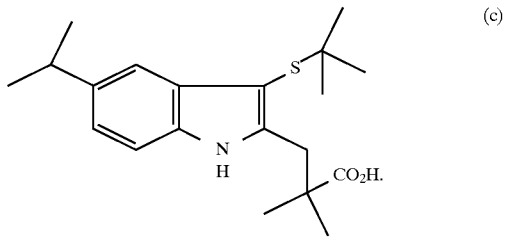

(c)

17. The compounds of structural formulae (IV) and (V):

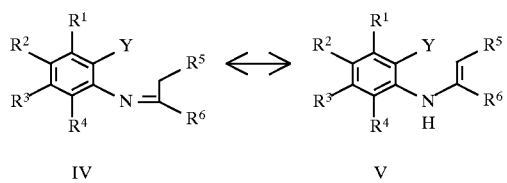

wherein $R^1, R^2, R^3, R^4, R^5, R^6$ and Y are as defined in claim 1.

18. The compounds of structural formulae (IV) and (V):

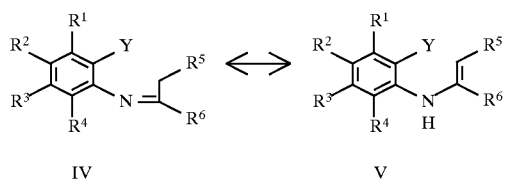

wherein $R^1, R^2, R^3, R^4, R^5, R^6$ and Y are as defined in claim 1.

* * * * *